United States Patent
Harlan et al.

(10) Patent No.: US 9,604,893 B2
(45) Date of Patent: Mar. 28, 2017

(54) PROTECTING PHENOL GROUPS

(71) Applicant: Univation Technologies, LLC, Houston, TX (US)

(72) Inventors: C. Jeff Harlan, Houston, TX (US); Steven D. Brown, League City, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 14/895,792

(22) PCT Filed: May 12, 2014

(86) PCT No.: PCT/US2014/037634
§ 371 (c)(1),
(2) Date: Dec. 3, 2015

(87) PCT Pub. No.: WO2014/197169
PCT Pub. Date: Dec. 11, 2014

(65) Prior Publication Data
US 2016/0122270 A1  May 5, 2016

Related U.S. Application Data

(60) Provisional application No. 61/831,503, filed on Jun. 5, 2013.

(51) Int. Cl.
| C08F 2/00 | (2006.01) |
|---|---|
| C08F 4/60 | (2006.01) |
| C07D 315/00 | (2006.01) |
| C07C 41/00 | (2006.01) |
| C07C 41/18 | (2006.01) |
| C07D 309/30 | (2006.01) |
| C07B 51/00 | (2006.01) |
| C07C 41/01 | (2006.01) |
| C07D 309/12 | (2006.01) |
| C08F 210/02 | (2006.01) |

(52) U.S. Cl.
CPC .............. *C07C 41/18* (2013.01); *C07B 51/00* (2013.01); *C07C 41/01* (2013.01); *C07D 309/12* (2013.01); *C07D 309/30* (2013.01); *C08F 210/02* (2013.01)

(58) Field of Classification Search
CPC .... C07D 309/30; C07D 309/12; C07B 51/00; C08F 210/02; C07C 41/18; C07C 41/01
USPC .......... 526/209; 502/162; 549/416; 568/644
See application file for complete search history.

(56) References Cited

U.S. PATENT DOCUMENTS 7,345,126 B2 *   3/2008   Inaba ........................ C08F 8/00
525/286

OTHER PUBLICATIONS

International Search Report & Written Opinion for related PCT Application PCT/US2014/037634, mailed Jul. 28, 2014 (7 pgs).

(Continued)

*Primary Examiner* — William Cheung
(74) *Attorney, Agent, or Firm* — Brooks, Cameron & Huebsch, PLLC

(57) ABSTRACT

A method for protecting a phenol group on a precursor compound is provided. The method includes reacting the phenol group with dihydropyran in an acid catalyzed protection reaction and quenching the protection reaction with a strong base within less than about 60 seconds to form a protected precursor compound.

20 Claims, 7 Drawing Sheets

(56) References Cited

OTHER PUBLICATIONS

Heravi, et al., "Solvent Free Tetrahydropyranylation of Alcohols and Phenols over Sulfuric Acid Adsorbed on Silica Gel" Synthetic Communications: An International Journal for Rapid Communication of Synthetic Organic Chemistry, 29:6, 1013-1016 (1999) (6 pgs).

\* cited by examiner

400

PROTECTING PHENOL GROUPS

This application is a National Stage Application under 35 U.S.C. §371 of International Application Number PCT/US2014/037634, filed May 12, 2014 and published as WO 2014/197169 on Dec. 11, 2014, which claims the benefit to U.S. Provisional Application 61/831,503, filed Jun. 5, 2013, the entire contents of which are incorporated herein by reference in its entirety.

BACKGROUND

Ethylene alpha-olefin (polyethylene) copolymers are typically produced in a low pressure reactor, utilizing, for example, solution, slurry, or gas phase polymerization processes. Polymerization takes place in the presence of catalyst systems such as those employing, for example, a Ziegler-Natta catalyst, a chromium based catalyst, a metallocene catalyst, or combinations thereof.

A number of catalyst compositions containing single site, e.g., metallocene, catalysts have been used to prepare polyethylene copolymers, producing relatively homogeneous copolymers at good polymerization rates. In contrast to traditional Ziegler-Natta catalyst compositions, single site catalyst compositions, such as metallocene catalysts, are catalytic compounds in which each catalyst molecule contains one or only a few polymerization sites.

Many catalyst systems have complex ligands around a catalytic metal site. The ligands are selected to determine the final properties of the polymer formed from the catalyst. For example, different ligands may change the productivity of the catalyst, the polymer chain lengths formed before termination, the rate of incorporation of comonomers, and the like. These ligands may function by modifying the physical environment around the catalytic metal site, for example, increasing the steric hindrance around the catalytic metal site, among others.

Control of these properties is obtained for the most part by the choice of the catalyst system. Thus, the catalyst design is important for producing polymers that are attractive from a commercial standpoint. Accordingly, improved techniques for synthesizing catalyst ligands are desirable.

SUMMARY

An embodiment described here provides a method for protecting a phenol group on a precursor compound. The method includes reacting the phenol group with dihydropyran in an acid catalyzed protection reaction and quenching the protection reaction with a strong base within less than about 60 seconds to form a protected precursor compound.

Another embodiment provides a method for forming a polymerization catalyst. The method includes reacting a phenol group on a precursor compound with dihydropyran to form a protected phenol precursor. The reaction is quenched with a strong base within less than about 60 seconds. An additional reaction is performed with the protected phenol precursor and a reagent to form a ligand precursor compound, wherein the reagent would attack an unprotected phenol group. The phenol is then deprotected on the ligand precursor compound.

Another embodiment provides a method for generating a polyethylene polymer. The method includes reacting at least ethylene with a catalyst system that includes a catalyst formed by reacting a metal compound with a ligand. The ligand is formed in a reaction sequence that includes reacting a phenol group on a precursor compound with dihydropyran to form a protected phenol precursor, and quenching the reaction with a strong base within less than about 60 seconds. The reaction sequence also includes performing an additional reaction with the protected phenol precursor and a reagent to form a ligand precursor compound, wherein the reagent would attack an unprotected phenol group and deprotecting the phenol on the ligand precursor compound to form the ligand.

DETAILED DESCRIPTION

Figure 1:
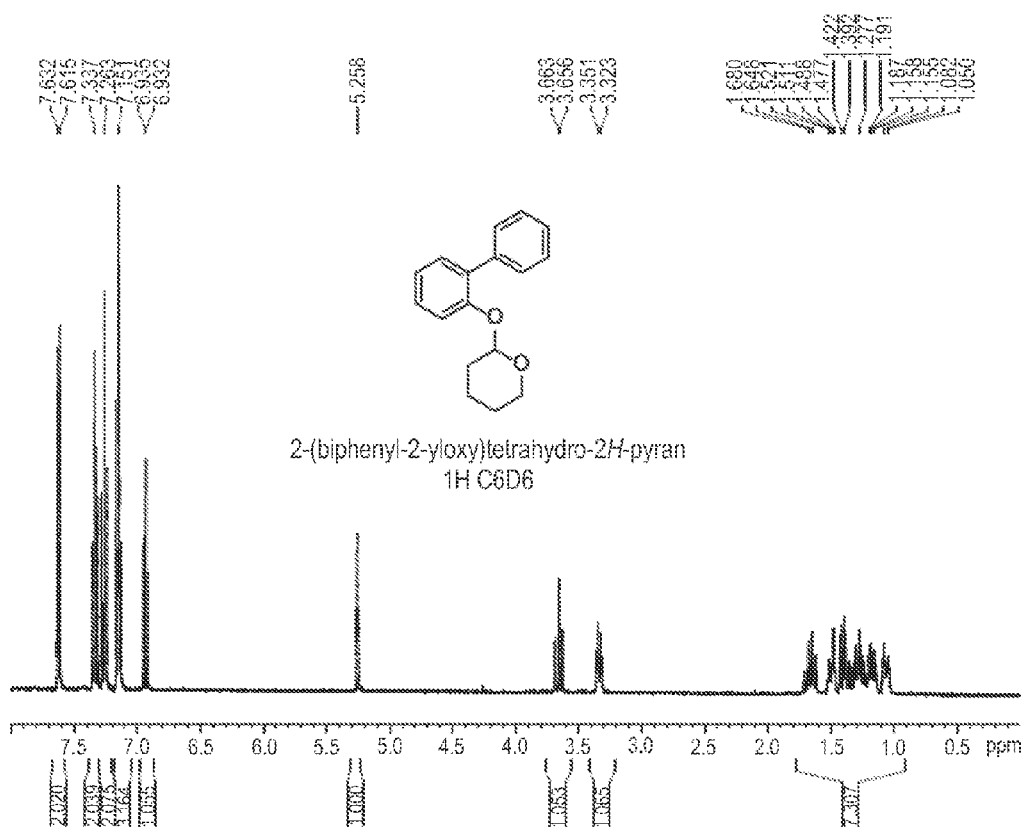
FIG. 1 is a plot showing the proton nuclear magnetic resonance ($^1$H NMR; 400 MHz; $C_6D_6$) spectrum obtained for the 2-(biphenyl-2-yloxy)tetrahydro-2H-pyran.

Forming ligands that may be used to make catalysts can often be problematic, as many precursors used in syntheses will participate in undesirable reactions with reagents. For example, one class of catalyst precursors that has been studied for forming catalysts are known as biphenylphenols, which have three or more aromatic groups attached to each other. Typically during the construction of these molecules it is necessary to protect one or more aromatic hydroxyl groups by converting them into less reactive species to allow other reactions to occur, and then deprotecting them during a later step.

Generally, protection reactions have used the protecting groups MOM (methoxymethyl) and THP (tetrahydropyran) during these syntheses. THP is the preferred protecting group because it avoids the use of hazardous compounds that are used for the MOM protection. A simple method for protecting aromatic hydroxyl groups with THP is the acid catalyzed addition of the hydroxyl group across the double bond of dihydropyran (DHP). Typical literature procedures use HCl, PTSA (para-toluenesulfonic acid), or pyridinium p-toluenesulfonate as the acid catalyst and extended reaction times (3 hours plus) followed by an aqueous workup employing base to neutralize the acid catalyst. Chromatography is often used for purification of the product. Examples of compounds, such as ligands, that may be produced using embodiments of the current techniques include the structures (I)-(III), below.

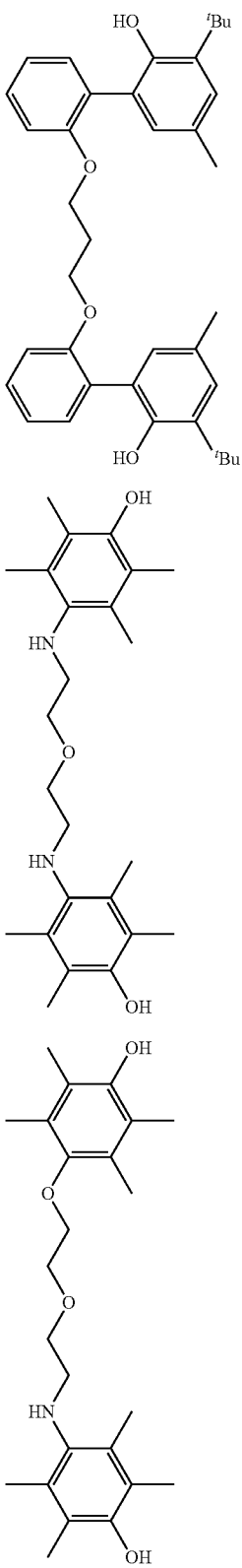

(I)

(II)

(III)

Although past research studies have recommended longer reaction times for the protection reaction to allow for complete reactions, extended reaction times for acid catalyzed addition of hydroxyl group across the double bond of dihydropyran can actually lead to decreased yields of the desired THP protected aromatic hydroxyl. The lower yields may be caused by a decomposition reaction of the initially formed product that allows it to revert back to the starting material and other degradation products. In embodiments described herein, this problem is mitigated by employing short reaction times for the acid catalyzed reactions, such as 120 seconds, 60 seconds, 30 seconds, or 10 seconds, followed by quenching with a strong base. The procedure leads to substantially pure products that require minimal purification steps. In the experimental section below, examples are provided for two methods of THP protection. An example of the overall procedure can be summarized by reaction (1). It can be noted, however, that the alcohol is not limited to the structure shown, as any aromatic alcohol group or groups may be protected using embodiments described herein.

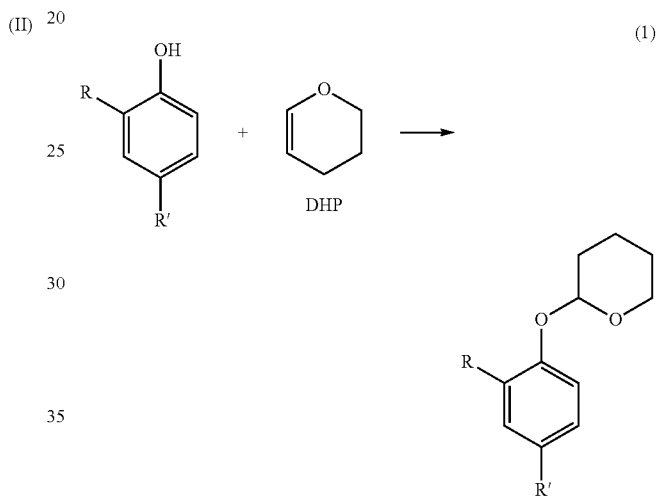

(1)

The timing of this reaction in comparison to the previous reactions is summarized in Table 1.

TABLE 1

| Reactions times and product purity for embodiments | | |
|---|---|---|
| | Previous Protection Schemes | Embodiments disclosed herein |
| Reaction Times | Hours to days | Seconds |
| Purity | Typically about 40%-90% | 99+% |

The ligands may be used to form various catalysts that can be used in catalyst systems and components to generate polymers of various compositions, including polyolefin homopolymers and copolymers. Potential reactions and catalysts are discussed in the sections to follow. However, it can be noted that the protection and deprotection reactions are not limited to ligand formation reactions, as described in examples herein, but can be used in any reaction scheme that needs to protect a phenol to allow other reactions to occur. These reactions schemes can include reactions to form ligands for catalysts, as well as other products, such as pharmaceuticals, among others.

The first section discusses catalyst compounds that can be used in embodiments, including non-metallocene catalysts, among others. The second section discusses catalyst forms that may be used in embodiments. The third section discusses supports that may be used. The fourth section discusses catalyst activators that may be used. The fifth section describes continuity additives and static control agents that may be used. Potential polymerization processes are discussed in the sixth section. Examples of the implementation of the procedures discussed in incorporated into a seventh section.

Catalyst Compounds
Metallocene Catalyst Compounds

Metallocene catalyst compounds are generally described 1 & 2 METALLOCENE-BASED POLYOLEFINS (John Scheirs & W. Kaminsky eds., John Wiley & Sons, Ltd. 2000); G. G. Hlatky in 181 COORDINATION CHEM. REV. 243-296 (1999); and, in particular, for use in the synthesis of polyethylene in 1 METALLOCENE-BASED POLYOLE-FINS 261-377 (2000). The metallocene catalyst compounds can include "half sandwich" and/or "full sandwich" compounds having one or more Cp ligands (cyclopentadienyl and ligands isolobal to cyclopentadienyl) bound to at least one Group 3 to Group 12 metal atom, and one or more leaving group(s) bound to the at least one metal atom. As used herein, all references to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

The Cp ligands are one or more rings or ring system(s), at least a portion of which includes i-bonded systems, such as cycloalkadienyl ligands and heterocyclic analogues. The ring(s) or ring system(s) typically include atoms selected from the group consisting of Groups 13 to 16 atoms, and, in a particular exemplary embodiment, the atoms that make up the Cp ligands are selected from the group consisting of carbon, nitrogen, oxygen, silicon, sulfur, phosphorous, germanium, boron, aluminum, and combinations thereof, where carbon makes up at least 50% of the ring members. In a more particular exemplary embodiment, the Cp ligand(s) are selected from the group consisting of substituted and unsubstituted cyclopentadienyl ligands and ligands isolobal to cyclopentadienyl, non-limiting examples of which include cyclopentadienyl, indenyl, fluorenyl and other structures. Further non-limiting examples of such ligands include cyclopentadienyl, cyclopentaphenanthreneyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated versions thereof (e.g., 4,5,6,7-tetrahydroindenyl, or "H$_4$ Ind"), substituted versions thereof (as discussed and described in more detail below), and heterocyclic versions thereof.

The metal atom "M" of the metallocene catalyst compound can be selected from the group consisting of Groups 3 through 12 atoms and lanthanide Group atoms in one exemplary embodiment; and selected from the group consisting of Groups 3 through 10 atoms in a more particular exemplary embodiment; and selected from the group consisting of Sc, Ti, Zr, Hf, V, Nb, Ta, Mn, Re, Fe, Ru, Os, Co, Rh, Ir, and Ni in yet a more particular exemplary embodiment; and selected from the group consisting of Groups 4, 5, and 6 atoms in yet a more particular exemplary embodiment; and Ti, Zr, Hf atoms in yet a more particular exemplary embodiment; and Zr in yet a more particular exemplary embodiment. The oxidation state of the metal atom "M" can range from 0 to +7 in one exemplary embodiment; and in a more particular exemplary embodiment, can be +1, +2, +3, +4, or +5; and in yet a more particular exemplary embodiment can be +2, +3 or +4. The groups bound to the metal atom "M" are such that the compounds described below in the formulas and structures are electrically neutral, unless otherwise indicated. The Cp ligand forms at least one chemical bond with the metal atom M to form the "metallocene catalyst compound." The Cp ligands are distinct from the leaving groups bound to the catalyst compound in that they are not highly susceptible to substitution/abstraction reactions.

The one or more metallocene catalyst compounds can be represented by the structure (VI):

$$Cp^A Cp^B MX_n \qquad (VI)$$

in which M is as described above; each X is chemically bonded to M; each Cp group is chemically bonded to M; and n is 0 or an integer from 1 to 4, and either 1 or 2 in a particular exemplary embodiment.

The ligands represented by $Cp^A$ and $Cp^B$ in structure (VI) can be the same or different cyclopentadienyl ligands or ligands isolobal to cyclopentadienyl, either or both of which can contain heteroatoms and either or both of which can be substituted by a group R. In at least one specific embodiment, $Cp^A$ and $Cp^B$ are independently selected from the group consisting of cyclopentadienyl, indenyl, tetrahydroindenyl, fluorenyl, and substituted derivatives of each.

Independently, each $Cp^A$ and $Cp^B$ of structure (VI) can be unsubstituted or substituted with any one or combination of substituent groups R. Non-limiting examples of substituent groups R as used in structure (VI) as well as ring substituents in structures discussed and described below, include groups selected from the group consisting of hydrogen radicals, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbamoyls, alkyl- and dialkyl-carbamoyls, acyloxys, acylaminos, aroylaminos, and combinations thereof. More particular non-limiting examples of alkyl substituents R associated with structures (VI) through (XI) include methyl, ethyl, propyl, butyl, pentyl, hexyl, cyclopentyl, cyclohexyl, benzyl, phenyl, methylphenyl, and tert-butylphenyl groups and the like, including all their isomers, for example, tertiary-butyl, isopropyl, and the like. Other possible radicals include substituted alkyls and aryls such as, for example, fluoromethyl, fluroethyl, difluroethyl, iodopropyl, bromohexyl, chlorobenzyl, hydrocarbyl substituted organometalloid radicals including trimethylsilyl, trimethylgermyl, methyldiethylsilyl, and the like, and halocarbyl-substituted organometalloid radicals, including tris(trifluoromethyl)silyl, methylbis(difluoromethyl)silyl, bromomethyldimethylgermyl and the like; and disubstituted boron radicals including dimethylboron, for example; and disubstituted Group 15 radicals including dimethylamine, dimethylphosphine, diphenylamine, methylphenylphosphine, as well as Group 16 radicals including methoxy, ethoxy, propoxy, phenoxy, methylsulfide and ethylsulfide. Other substituent groups R include, but are not limited to, olefins such as olefinically unsaturated substituents including vinyl-terminated ligands such as, for example, 3-butenyl, 2-propenyl, 5-hexenyl, and the like. In one exemplary embodiment, at least two R groups (two adjacent R groups in a particular exemplary embodiment) are joined to form a ring structure having from 3 to 30 atoms selected from the group consisting of carbon, nitrogen, oxygen, phosphorous, silicon, germanium, aluminum, boron, and combinations thereof. Also, a substituent group R such as 1-butanyl can form a bonding association to the element M.

Each leaving group, or X, in the structure (VI) above and for the structures in (VII) through (IX) below is independently selected from the group consisting of: halogen ions, hydrides, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_8$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof, in a more particular exemplary embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular exemplary embodiment; hydride, chloride, fluoride, methyl, phenyl, phenoxy, benzoxy, tosyl, fluoromethyls and fluorophenyls, in yet a more particular exemplary embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls, and $C_1$ to $C_{12}$ heteroatom-containing alkylaryls, in yet a more particular exemplary embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls, in yet a more particular exemplary embodiment; chloride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls), in yet a more particular exemplary embodiment.

Other non-limiting examples of X groups include amines, phosphines, ethers, carboxylates, dienes, hydrocarbon radicals having from 1 to 20 carbon atoms, fluorinated hydrocarbon radicals (e.g., —$C_6F_5$ (pentafluorophenyl)), fluorinated alkylcarboxylates (e.g., $CF_3C(O)O^-$), hydrides, halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one exemplary embodiment, two or more X's form a part of a fused ring or ring system. In at least one specific embodiment, X can be a leaving group selected from the group consisting of chloride ions, bromide ions, $C_1$ to $C_{10}$ alkyls, and $C_2$ to $C_{12}$ alkenyls, carboxylates, acetylacetonates, and alkoxides.

The metallocene catalyst compound includes those of structure (VI) where $Cp^A$ and $Cp^B$ are bridged to each other by at least one bridging group, (A), such that the structure is represented by structure (VII):

$Cp^A(A)Cp^BMX_n$          (VII)

These bridged compounds represented by structure (VII) are known as "bridged metallocenes." The elements $Cp^A$, $Cp^B$, M, X and n in structure (VII) are as defined above for structure (VI); where each Cp ligand is chemically bonded to M, and (A) is chemically bonded to each Cp. The bridging group (A) can include divalent hydrocarbon groups containing at least one Group 13 to 16 atom, such as, but not limited to, at least one of a carbon, oxygen, nitrogen, silicon, aluminum, boron, germanium, tin atom, and combinations thereof; where the heteroatom can also be $C_1$ to $C_{12}$ alkyl or aryl substituted to satisfy neutral valency. In at least one specific embodiment, the bridging group (A) can also include substituent groups R as defined above (for structure (VI)) including halogen radicals and iron. In at least one specific embodiment, the bridging group (A) can be represented by $C_1$ to $C_6$ alkylenes, substituted $C_1$ to $C_6$ alkylenes, oxygen, sulfur, $R'_2C=$, $R'_2Si=$, $=Si(R')_2Si(R'_2)=$, $R'_2Ge=$, and $R'P=$, where "=" represents two chemical bonds, R' is independently selected from the group consisting of hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and where two or more R' can be joined to form a ring or ring system. In at least one specific embodiment, the bridged metallocene catalyst compound of structure (VII) includes two or more bridging groups (A). In one or more embodiments, (A) can be a divalent bridging group bound to both $Cp^A$ and $Cp^B$ selected from the group consisting of divalent $C_1$ to $C_{20}$ hydrocarbyls and $C_1$ to $C_{20}$ heteroatom containing hydrocarbonyls, where the heteroatom containing hydrocarbonyls include from one to three heteroatoms.

The bridging group (A) can include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties where the Si atom is replaced by a Ge or a C atom; as well as dimethylsilyl, diethylsilyl, dimethylgermyl and diethylgermyl.

The bridging group (A) can also be cyclic, having, for example, 4 to 10 ring members; in a more particular exemplary embodiment, bridging group (A) can have 5 to 7 ring members. The ring members can be selected from the elements mentioned above, and, in a particular embodiment, can be selected from one or more of B, C, Si, Ge, N, and O. Non-limiting examples of ring structures which can be present as, or as part of, the bridging moiety are cyclobutylidene, cyclopentylidene, cyclohexylidene, cycloheptylidene, cyclooctylidene and the corresponding rings where one or two carbon atoms are replaced by at least one of Si, Ge, N and O. In one or more embodiments, one or two carbon atoms can be replaced by at least one of Si and Ge. The bonding arrangement between the ring and the Cp groups can be cis-, trans-, or a combination thereof.

The cyclic bridging groups (A) can be saturated or unsaturated and/or can carry one or more substituents and/or can be fused to one or more other ring structures. If present, the one or more substituents can be, in at least one specific embodiment, selected from the group consisting of hydrocarbyl (e.g., alkyl, such as methyl) and halogen (e.g., F, Cl). The one or more Cp groups to which the above cyclic bridging moieties can optionally be fused can be saturated or unsaturated, and are selected from the group consisting of those having 4 to 10, more particularly 5, 6, or 7 ring members (selected from the group consisting of C, N, O, and S in a particular exemplary embodiment) such as, for example, cyclopentyl, cyclohexyl and phenyl. Moreover, these ring structures can themselves be fused such as, for example, in the case of a naphthyl group. Moreover, these (optionally fused) ring structures can carry one or more substituents. Illustrative, non-limiting examples of these substituents are hydrocarbyl (particularly alkyl) groups and halogen atoms. The ligands $Cp^A$ and $Cp^B$ of structure (VI) and (VII) can be different from each other. The ligands $Cp^A$ and $Cp^B$ of structure (VI) and (VII) can be the same.

The metallocene catalyst compound can include bridged mono-ligand metallocene compounds (e.g., mono cyclopentadienyl catalyst components). Exemplary metallocene catalyst compounds are further described in U.S. Pat. No. 6,943,134.

It is contemplated that the metallocene catalyst components discussed and described above include their structural or optical or enantiomeric isomers (racemic mixture), and, in one exemplary embodiment, can be a pure enantiomer. As used herein, a single, bridged, asymmetrically substituted metallocene catalyst compound having a racemic and/or meso isomer does not, itself, constitute at least two different bridged, metallocene catalyst components.

The amount of the transition metal component of the one or more metallocene catalyst compounds in the catalyst system can range from a low of about 0.2 wt. %, about 3 wt. %, about 0.5 wt. %, or about 0.7 wt. % to a high of about 1 wt. %, about 2 wt. %, about 2.5 wt. %, about 3 wt. %, about 3.5 wt. %, or about 4 wt. %, based on the total weight of the catalyst system.

The metallocene catalyst compounds can include any combination of any embodiment discussed and described herein. For example, the metallocene catalyst compound can include, but is not limited to, bis(n-butylcyclopentadienyl) zirconium $(CH_3)_2$, bis(n-butylcyclopentadienyl) zirconium $Cl_2$, bis(n-butylcyclopentadienyl) zirconium $Cl_2$, (n-propylcyclopentadienyl, tetramethylcyclopentadienyl) zirconium $Cl_2$, [(pentamethylbenzylNCH$_2$)$_2$NH]ZrPh$_2$, [(pentamethylbenzylNCH$_2$)$_2$O]ZrPh$_2$, or any combinations thereof.

In addition to the metallocene catalyst compounds discussed and described above, other suitable metallocene catalyst compounds can include, but are not limited to, metallocenes discussed and described in U.S. Pat. Nos. 7,741,417; 7,179,876; 7,169,864; 7,157,531; 7,129,302; 6,995,109; 6,958,306; 6,884,748; 6,689,847; and WO Publications: WO 1997/022635; WO 1998/046651; WO 2000/069922; WO 2001/030860; WO 2001/030861; WO 2002/046246; WO 2002/050088; WO 2004/026921; and WO 06/019494.

Although the catalyst compounds may be written or shown with methyl-, chloro-, or phenyl- leaving groups attached to the central metal, it can be understood that these groups may be different without changing the catalyst involved. For example, each of these ligands may independently be a phenyl group (Ph), a methyl group (Me), a chloro group (Cl), a fluoro group (F), or any number of other groups, including organic groups, or heteroatom groups. Further, these ligands will change during the reaction, as a pre-catalyst is converted to the active catalyst for the reaction.

Group 15 Atom and Non-Metallocene Catalyst Compounds

The catalyst system can include one or more Group 15 metal-containing catalyst compounds. As used herein, these are termed non-metallocene catalyst compounds. The Group 15 metal-containing compound generally includes a Group 3 to 14 metal atom, a Group 3 to 7, or a Group 4 to 6 metal atom. In many embodiments, the Group 15 metal-containing compound includes a Group 4 metal atom bound to at least one leaving group and also bound to at least two Group 15 atoms, at least one of which is also bound to a Group 15 or 16 atom through another group.

In one or more embodiments, at least one of the Group 15 atoms is also bound to a Group 15 or 16 atom through another group which may be a $C_1$ to $C_{20}$ hydrocarbon group, a heteroatom containing group, silicon, germanium, tin, lead, or phosphorus, wherein the Group 15 or 16 atom may also be bound to nothing or a hydrogen, a Group 14 atom containing group, a halogen, or a heteroatom containing group, and wherein each of the two Group 15 atoms are also bound to a cyclic group and can optionally be bound to hydrogen, a halogen, a heteroatom or a hydrocarbyl group, or a heteroatom containing group.

The Group 15-containing metal compounds can be described more particularly with structures (VIII) or (IX):

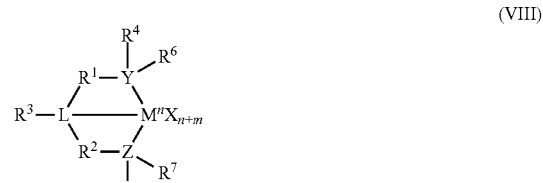

(VIII)

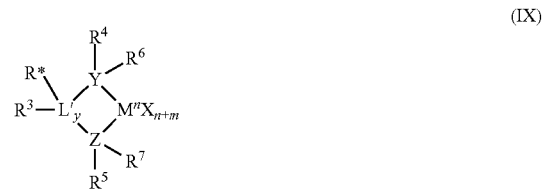

(IX)

where M is a Group 3 to 12 transition metal or a Group 13 or 14 main group metal, a Group 4, 5, or 6 metal. In many embodiments, M is a Group 4 metal, such as zirconium, titanium, or hafnium. Each X is independently a leaving group, such as an anionic leaving group. The leaving group may include a hydrogen, a hydrocarbyl group, a heteroatom, a halogen, or an alkyl; y is 0 or 1 (when y is 0 group L' is absent). The term 'n' is the oxidation state of M. In various embodiments, n is +3, +4, or +5. In many embodiments, n is +4. The term 'm' represents the formal charge of the YZL or the YZL' ligand, and is 0, −1, −2 or −3 in various embodiments. In many embodiments, m is −2. L is a Group 15 or 16 element, such as nitrogen or oxygen; L' is a Group 15 or 16 element or Group 14 containing group, such as carbon, silicon or germanium. Y is a Group 15 element, such as nitrogen or phosphorus. In many embodiments, Y is nitrogen. Z is a Group 15 element, such as nitrogen or phosphorus. In many embodiments, Z is nitrogen. $R^1$ and $R^2$ are, independently, a $C_1$ to $C_{20}$ hydrocarbon group, a heteroatom containing group having up to twenty carbon atoms, silicon, germanium, tin, lead, or phosphorus. In many embodiments, $R^1$ and $R^2$ are a $C_2$ to $C_{20}$ alkyl, aryl or aralkyl group, such as a linear, branched or cyclic $C_2$ to $C_{20}$ alkyl group, or a $C_2$ to $C_6$ hydrocarbon group, such as the X described with respect to structures (VI) and (VII) above. $R^1$ and $R^2$ may also be interconnected to each other. $R^3$ may be absent or may be a hydrocarbon group, a hydrogen, a halogen, a heteroatom containing group. In many embodiments, $R^3$ is absent, for example, if L is an oxygen, or a hydrogen, or a linear, cyclic, or branched alkyl group having 1 to 20 carbon atoms. $R^4$ and $R^5$ are independently an alkyl group, an aryl group, substituted aryl group, a cyclic alkyl group, a substituted cyclic alkyl group, a cyclic aralkyl group, a substituted cyclic aralkyl group, or multiple ring system, often having up to 20 carbon atoms. In many embodiments, $R^4$ and $R^5$ have between 3 and 10 carbon atoms, or are a $C_1$ to $C_{20}$ hydrocarbon group, a $C_1$ to $C_{20}$ aryl group or a $C_1$ to $C_{20}$ aralkyl group, or a heteroatom containing group. $R^4$ and $R^5$ may be interconnected to each other. $R^6$ and $R^2$ are independently absent, hydrogen, an alkyl group, halogen, heteroatom, or a hydrocarbyl group, such as a linear, cyclic or branched alkyl group having 1 to 20 carbon atoms. In many embodiments, $R^6$ and $R^7$ are absent. R* may be absent, or may be a hydrogen, a Group 14 atom containing group, a halogen, or a heteroatom containing group.

By "formal charge of the YZL or YZL' ligand," it is meant the charge of the entire ligand absent the metal and the leaving groups X. By "$R^1$ and $R^2$ may also be interconnected" it is meant that $R^1$ and $R^2$ may be directly bound to each other or may be bound to each other through other groups. By "$R^4$ and $R^5$ may also be interconnected" it is meant that $R^4$ and $R^5$ may be directly bound to each other or may be bound to each other through other groups. An alkyl group may be linear, branched alkyl radicals, alkenyl radicals, alkynyl radicals, cycloalkyl radicals, aryl radicals, acyl radicals, aroyl radicals, alkoxy radicals, aryloxy radicals, alkylthio radicals, dialkylamino radicals, alkoxycarbonyl radicals, aryloxycarbonyl radicals, carbamoyl radicals, alkyl- or dialkyl-carbamoyl radicals, acyloxy radicals, acylamino radicals, aroylamino radicals, straight, branched or cyclic, alkylene radicals, or combination thereof. An aralkyl group is defined to be a substituted aryl group.

In one or more embodiments, $R^4$ and $R^5$ are independently a group represented by the following structure (X).

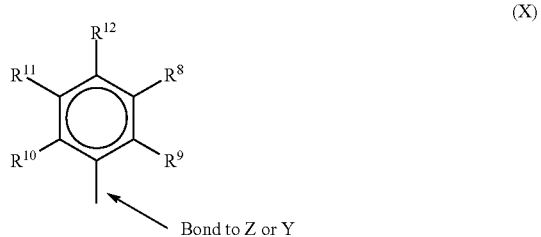

(X)

When $R^4$ and $R^5$ are as formula VII, $R^8$ to $R^{12}$ are each independently hydrogen, a $C_1$ to $C_{40}$ alkyl group, a halide, a heteroatom, a heteroatom containing group containing up to 40 carbon atoms. In many embodiments, $R^8$ to $R^{12}$ are a $C_1$ to $C_{20}$ linear or branched alkyl group, such as a methyl, ethyl, propyl, or butyl group. In embodiments, any of $R^8$ to $R^{12}$ can be a hydroxyl group. Any two of the R groups may form a cyclic group and/or a heterocyclic group. The cyclic groups may be aromatic. In one embodiment $R^9$, $R^{10}$ and $R^{12}$ are independently a methyl, ethyl, propyl, or butyl group (including all isomers). In another embodiment, $R^9$, $R^{10}$ and $R^{12}$ are methyl groups, and $R^8$ and $R^{11}$ are hydrogen.

In one or more embodiments, $R^4$ and $R^5$ are both a group represented by the following structure (XI).

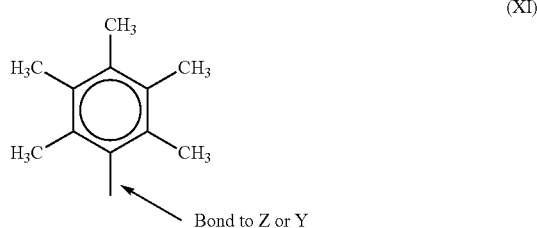

(XI)

When $R^4$ and $R^5$ follow structure (XI), M is a Group 4 metal, such as zirconium, titanium, or hafnium. In many embodiments, M is zirconium. Each of L, Y, and Z may be a nitrogen. Each of $R^1$ and $R^2$ may be —$CH_2$—$CH_2$—. $R^3$ may be hydrogen, and $R^6$ and $R^7$ may be absent.

The Group 15 metal-containing catalyst compound can be represented by structure (IV). In formula IV, Ph represents phenyl. Representative Group 15-containing metal compounds and preparation thereof can be as discussed and described in U.S. Pat. Nos. 5,318,935; 5,889,128; 6,333,389; 6,271,325; and 6,689,847; WO Publications WO 99/01460; WO 98/46651; WO 2009/064404; WO 2009/064452; and WO 2009/064482; and EP 0 893 454; and EP 0 894 005.

Catalyst Forms

The catalyst system may include a catalyst component in a slurry, which may have an initial catalyst compound, and an added solution catalyst component that is added to the slurry. Generally, a non-metallocene catalyst will be supported in the initial slurry, depending on solubility. However, in some embodiments, the initial catalyst component slurry may have no catalysts. In this case, two or more solution catalysts may be added to the slurry to cause each to be supported.

Any number of combinations of catalyst components may be used in embodiments. For example, the catalyst component slurry can include an activator and a support, or a supported activator. Further, the slurry can include a catalyst compound in addition to the activator and the support. As noted, the catalyst compound in the slurry may be supported.

The slurry may include one or more activators and supports, and one more catalyst compounds. For example, the slurry may include two or more activators (such as alumoxane and a modified alumoxane) and a catalyst compound, or the slurry may include a supported activator and more than one catalyst compounds. In one embodiment, the slurry includes a support, an activator, and two catalyst compounds. In another embodiment the slurry includes a support, an activator and two different catalyst compounds, which may be added to the slurry separately or in combination. The slurry, containing silica and alumoxane, may be contacted with a catalyst compound, allowed to react, and thereafter the slurry is contacted with another catalyst compound, for example, in a trim system.

The molar ratio of metal in the activator to metal in the catalyst compound in the slurry may be 1000:1 to 0.5:1, 300:1 to 1:1, or 150:1 to 1:1. The slurry can include a support material which may be any inert particulate carrier material known in the art, including, but not limited to, silica, fumed silica, alumina, clay, talc or other support materials such as disclosed above. In one embodiment, the slurry contains silica and an activator, such as methyl aluminoxane ("MAO"), modified methyl aluminoxane ("MMAO"), as discussed further below.

One or more diluents or carriers can be used to facilitate the combination of any two or more components of the catalyst system in the slurry or in the trim catalyst solution. For example, the single site catalyst compound and the activator can be combined together in the presence of toluene or another non-reactive hydrocarbon or hydrocarbon mixture to provide the catalyst mixture. In addition to toluene, other suitable diluents can include, but are not limited to, ethylbenzene, xylene, pentane, hexane, heptane, octane, other hydrocarbons, or any combination thereof. The support, either dry or mixed with toluene can then be added to the catalyst mixture or the catalyst/activator mixture can be added to the support.

The catalyst is not limited to a slurry arrangement, as a mixed catalyst system may be made on a support and dried. The dried catalyst system can then be fed to the reactor through a dry feed system.

Support

As used herein, the terms "support" and "carrier" are used interchangeably and refer to any support material, including a porous support material, such as talc, inorganic oxides, and inorganic chlorides. The one or more single site catalyst compounds of the slurry can be supported on the same or separate supports together with the activator, or the activator can be used in an unsupported form, or can be deposited on a support different from the single site catalyst compounds, or any combination thereof. This may be accomplished by any technique commonly used in the art. There are various other methods in the art for supporting a single site catalyst compound. For example, the single site catalyst compound can contain a polymer bound ligand as described in, for example, U.S. Pat. Nos. 5,473,202 and 5,770,755. The single site catalyst compounds of the slurry can be spray dried as described in, for example, U.S. Pat. No. 5,648,310. The support used with the single site catalyst compound can be functionalized, as described in EP 0 802 203, or at least one substituent or leaving group is selected as described in U.S. Pat. No. 5,688,880.

The support can be or include one or more inorganic oxides, for example, of Group 2, 3, 4, 5, 13, or 14 elements. The inorganic oxide can include, but is not limited to silica, alumina, titania, zirconia, boria, zinc oxide, magnesia, or any combination thereof. Illustrative combinations of inorganic oxides can include, but are not limited to, alumina-silica, silica-titania, alumina-silica-titania, alumina-zirconia, alumina-titania, and the like. The support can be or include silica, alumina, or a combination thereof. In one embodiment described herein, the support is silica.

Suitable commercially available silica supports can include, but are not limited to, ES757, ES70, and ES70W available from PQ Corporation. Suitable commercially available silica-alumina supports can include, but are not limited to, SIRAL® 1, SIRAL® 5, SIRAL® 10, SIRAL® 20, SIRAL® 28M, SIRAL® 30, and SIRAL® 40, available from SASOL®. Generally, catalysts supports comprising silica gels with activators, such as methylaluminoxanes (MAOs), are used in the trim systems described, since these supports may function better for cosupporting solution carried catalysts.

Suitable catalyst supports are discussed and described in Hlatky, Chem. Rev. (2000), 100, 1347 1376 and Fink et al., Chem. Rev. (2000), 100, 1377 1390, U.S. Pat. Nos. 4,701,432, 4,808,561, 4,912,075, 4,925,821, 4,937,217, 5,008,228, 5,238,892, 5,240,894, 5,332,706, 5,346,925, 5,422,325, 5,466,649, 5,466,766, 5,468,702, 5,529,965, 5,554,704, 5,629,253, 5,639,835, 5,625,015, 5,643,847, 5,665,665, 5,698,487, 5,714,424, 5,723,400, 5,723,402, 5,731,261, 5,759,940, 5,767,032 and 5,770,664, and WO 95/32995, WO 95/14044, WO 96/06187, and WO 97/02297.

Activator

As used herein, the term "activator" may refer to any compound or combination of compounds, supported, or unsupported, which can activate a single site catalyst compound or component, such as by creating a cationic species of the catalyst component. For example, this can include the abstraction of at least one leaving group (the "X" group in the single site catalyst compounds described herein) from the metal center of the single site catalyst compound/component. The activator may also be referred to as a "co-catalyst."

For example, the activator can include a Lewis acid or a non-coordinating ionic activator or ionizing activator, or any other compound including Lewis bases, aluminum alkyls, and/or conventional-type co-catalysts. In addition to methylaluminoxane ("MAO") and modified methylaluminoxane ("MMAO") mentioned above, illustrative activators can include, but are not limited to, aluminoxane or modified aluminoxane, and/or ionizing compounds, neutral or ionic, such as tri (n-butyl)ammonium tetrakis(pentafluorophenyl) boron, a trisperfluorophenyl boron metalloid precursor, a trisperfluoronaphthyl boron metalloid precursor, or any combinations thereof.

Aluminoxanes can be described as oligomeric aluminum compounds having —Al(R)—O— subunits, where R is an alkyl group. Examples of aluminoxanes include, but are not limited to, methylaluminoxane ("MAO"), modified methylaluminoxane ("MMAO"), ethylaluminoxane, isobutylaluminoxane, or a combination thereof. Aluminoxanes can be produced by the hydrolysis of the respective trialkylaluminum compound. MMAO can be produced by the hydrolysis of trimethylaluminum and a higher trialkylaluminum, such as triisobutylaluminum. MMAOs are generally more soluble in aliphatic solvents and more stable during storage. There are a variety of methods for preparing aluminoxane and modified aluminoxanes, non-limiting examples can be as discussed and described in U.S. Pat. Nos. 4,665,208; 4,952,540; 5,091,352; 5,206,199; 5,204,419; 4,874,734; 4,924,018; 4,908,463; 4,968,827; 5,308,815; 5,329,032; 5,248,801; 5,235,081; 5,157,137; 5,103,031; 5,391,793; 5,391,529; 5,693,838; 5,731,253; 5,731,451; 5,744,656; 5,847,177; 5,854,166; 5,856,256; and 5,939,346; and EP 0 561 476; EP 0 279 586; EP 0 594-218; and EP 0 586 665; and WO Publications WO 94/10180 and WO 99/15534.

As noted above, one or more organo-aluminum compounds such as one or more alkylaluminum compounds can be used in conjunction with the aluminoxanes. For example, alkylaluminum species that may be used are diethylaluminum ethoxide, diethylaluminum chloride, and/or diisobutylaluminum hydride. Examples of trialkylaluminum compounds include, but are not limited to, trimethylaluminum, triethylaluminum ("TEAL"), triisobutylaluminum ("TiBAl"), tri-n-hexylaluminum, tri-n-octylaluminum, tripropylaluminum, tributylaluminum, and the like.

Continuity Additive/Static Control Agent

In gas-phase polyethylene production processes, it may be desirable to use one or more static control agents to aid in regulating static levels in the reactor. As used herein, a static control agent is a chemical composition which, when introduced into a fluidized bed reactor, may influence or drive the static charge (negatively, positively, or to zero) in the fluidized bed. The specific static control agent used may depend upon the nature of the static charge, and the choice of static control agent may vary dependent upon the polymer being produced and the single site catalyst compounds being used. For example, the use of static control agents is disclosed in European Patent No. 0229368 and U.S. Pat. Nos. 4,803,251; 4,555,370; and 5,283,278, and references cited therein.

Control agents such as aluminum stearate may be employed. The static control agent used may be selected for its ability to receive the static charge in the fluidized bed without adversely affecting productivity. Other suitable static control agents may also include aluminum distearate, ethoxlated amines, and anti-static compositions such as those provided by Innospec Inc. under the trade name OCTASTAT. For example, OCTASTAT 2000 is a mixture of a polysulfone copolymer, a polymeric polyamine, and oil-soluble sulfonic acid.

Any of the aforementioned control agents, as well as those described in, for example, WO 2001/044322, listed under the heading Carboxylate Metal Salt and including those chemicals and compositions listed as antistatic agents may be employed either alone or in combination as a control agent. For example, the carboxylate metal salt may be combined with an amine containing control agent (e.g., a carboxylate metal salt with any family member belonging to the KEMAMINE® (available from Crompton Corporation) or ATMER® (available from ICI Americas Inc.) family of products).

Other useful continuity additives include ethyleneimine additives useful in embodiments disclosed herein may include polyethyleneimines having the following general formula:

in which n may be from about 10 to about 10,000. The polyethyleneimines may be linear, branched, or hyper-branched (e.g., forming dendritic or arborescent polymer structures). They can be a homopolymer or copolymer of ethyleneimine or mixtures thereof (referred to as polyethyl-eneimine(s) hereafter). Although linear polymers represented by the chemical formula —[$CH_2$—$CH_2$—NH]— may be used as the polyethyleneimine, materials having primary, secondary, and tertiary branches can also be used. Commercial polyethyleneimine can be a compound having branches of the ethyleneimine polymer.

Suitable polyethyleneimines are commercially available from BASF Corporation under the trade name Lupasol. These compounds can be prepared as a wide range of molecular weights and product activities. Examples of commercial polyethyleneimines sold by BASF suitable for use in the present invention include, but are not limited to, Lupasol FG and Lupasol WF.

Another useful continuity additive can include a mixture of aluminum distearate and an ethoxylated amine-type compound, e.g., IRGASTAT AS-990, available from Huntsman (formerly Ciba Specialty Chemicals). The mixture of aluminum distearate and ethoxylated amine type compound can be slurried in mineral oil e.g., Hydrobrite 380. For example, the mixture of aluminum distearate and an ethoxylated amine type compound can be slurried in mineral oil to have total slurry concentration of ranging from about 5 wt. % to about 50 wt. % or about 10 wt. % to about 40 wt. %, or about 15 wt. % to about 30 wt. %. Other useful static control agents and additives are disclosed in U.S. Patent Application Publication No. 2008/0045663.

The continuity additive(s) or static control agent(s) may be added to the reactor in an amount ranging from 0.05 to 200 ppm, based on the weight of all feeds to the reactor, excluding recycle. In some embodiments, the continuity additive may be added in an amount ranging from 2 to 100 ppm, or in an amount ranging from 4 to 50 ppm.

Polymerization Process

The catalyst system can be used to polymerize one or more olefins, such as ethylene, to provide one or more polymer products therefrom. Any suitable polymerization process can be used, including, but not limited to, high pressure, solution, slurry, and/or gas phase polymerization processes.

As used herein, the terms "polyethylene" and "polyethylene copolymer" refer to a polymer having at least 50 wt. % ethylene-derived units. In various embodiments, the polyethylene can have at least 70 wt. % ethylene-derived units, at least 80 wt. % ethylene-derived units, at least 90 wt. % ethylene-derived units, or at least 95 wt. % ethylene-derived units. The polyethylene polymers described herein are generally copolymer, but may also include terpolymers, having one or more other monomeric units. As described herein, a polyethylene can include, for example, at least one or more other olefins or comonomers. Suitable comonomers can contain 3 to 16 carbon atoms, from 3 to 12 carbon atoms, from 4 to 10 carbon atoms, and from 4 to 8 carbon atoms. Examples of comonomers include, but are not limited to, propylene, 1-butene, 1-pentene, 1-hexene, 1-heptene, 1-octene, 4-methylpent-1-ene, 1-decene, 1-dodecene, 1-hexadecene, and the like.

A gas phase polymerization may be conducted in a fluidized bed reactor which can include a reaction zone and a velocity reduction zone. The reaction zone can include a bed that includes growing polymer particles, formed polymer particles and a minor amount of catalyst particles fluidized by the continuous flow of the gaseous monomer and diluent to remove heat of polymerization through the reaction zone. Optionally, some of the re-circulated gases can be cooled and compressed to form liquids that increase the heat removal capacity of the circulating gas stream when readmitted to the reaction zone. A suitable rate of gas flow can be readily determined by experimentation. Make-up of gaseous monomer to the circulating gas stream can be at a rate equal to the rate at which particulate polymer product and monomer associated therewith is withdrawn from the reactor and the composition of the gas passing through the reactor can be adjusted to maintain an essentially steady state gaseous composition within the reaction zone. The gas leaving the reaction zone can be passed to the velocity reduction zone where entrained particles are removed, for example, by slowing and falling back to the reaction zone. If desired, finer entrained particles and dust can be removed in a separation system, such as a cyclone and/or fines filter. The gas can be passed through a heat exchanger where at least a portion of the heat of polymerization can be removed. The gas can then be compressed in a compressor and returned to the reaction zone. Additional reactor details and means for operating the reactor are described in, for example, U.S. Pat. Nos. 3,709,853; 4,003,712; 4,011,382; 4,302,566; 4,543,399; 4,882,400; 5,352,749; and 5,541,270; EP 0802202; and Belgian Patent No. 839,380.

The reactor temperature of the fluid bed process can be greater than about 30° C., about 40° C., about 50° C., about 90° C., about 100° C., about 110° C., about 120° C., about 150° C., or higher. In general, the reactor temperature is operated at the highest feasible temperature taking into account the sintering temperature of the polymer product within the reactor. Thus, the upper temperature limit in one embodiment is the melting temperature of the polyethylene copolymer produced in the reactor. However, higher temperatures may result in narrower MWDs, which can be improved by the addition of structure (IV), or other co-catalysts, as described herein.

Hydrogen gas can be used in olefin polymerization to control the final properties of the polyolefin, such as described in the "Polypropylene Handbook," at pages 76-78 (Hanser Publishers, 1996). Using certain catalyst systems, increasing concentrations (partial pressures) of hydrogen can increase the flow index (FI), or melt index (MI) of the polyethylene copolymer generated. The flow index can thus be influenced by the hydrogen concentration. The amount of hydrogen in the polymerization can be expressed as a mole ratio relative to the total polymerizable monomer, for example, ethylene, or a blend of ethylene and hexene or propylene.

The amount of hydrogen used in the polymerization process can be an amount necessary to achieve the desired flow index of the final polyolefin polymer. For example, the mole ratio of hydrogen to total monomer ($H_2$:monomer) can be greater than about 0.0001, greater than about 0.0005, or greater than about 0.001. Further, the mole ratio of hydrogen to total monomer ($H_2$:monomer) can be less than about 10, less than about 5, less than about 3, and less than about 0.10. A desirable range for the mole ratio of hydrogen to monomer can include any combination of any upper mole ratio limit with any lower mole ratio limit described herein. Expressed another way, the amount of hydrogen in the reactor at any time can range to up to about 5,000 ppm, up to about 4,000 ppm in another embodiment, up to about 3,000 ppm, or between about 50 ppm and 5,000 ppm, or between about 50 ppm and 2,000 ppm in another embodiment. The amount of hydrogen in the reactor can range from a low of about 1 ppm, about 50 ppm, or about 100 ppm to a high of about 400 ppm, about 800 ppm, about 1,000 ppm, about 1,500 ppm, or about 2,000 ppm, based on weight. Further, the ratio of hydrogen to total monomer ($H_2$:monomer) can be about 0.00001:1 to about 2:1, about 0.005:1 to about 1.5:1, or about 0.0001:1 to about 1:1. The one or more reactor pressures in a gas phase process (either single stage or two or more stages) can vary from 690 kPa (100 psig) to 3,448 kPa (500 psig), in the range from 1,379 kPa (200 psig) to 2,759 kPa (400 psig), or in the range from 1,724 kPa (250 psig) to 2,414 kPa (350 psig).

The gas phase reactor can be capable of producing from about 10 kg of polymer per hour (25 lbs/hr) to about 90,900 kg/hr (200,000 lbs/hr), or greater, and greater than about 455 kg/hr (1,000 lbs/hr), greater than about 4,540 kg/hr (10,000 lbs/hr), greater than about 11,300 kg/hr (25,000 lbs/hr), greater than about 15,900 kg/hr (35,000 lbs/hr), and greater than about 22,700 kg/hr (50,000 lbs/hr), and from about 29,000 kg/hr (65,000 lbs/hr) to about 45,500 kg/hr (100,000 lbs/hr).

A slurry polymerization process may be used to prepare polymer in embodiments. A slurry polymerization process generally uses pressures in the range of from about 101 kPa (1 atmosphere) to about 5,070 kPa (50 atmospheres) or greater, and temperatures in the range of from about 0° C. to about 120° C., and more particularly from about 30° C. to about 100° C. In a slurry polymerization, a suspension of solid, particulate polymer can be formed in a liquid polymerization diluent medium to which ethylene, comonomers, and hydrogen along with catalyst can be added. The suspension including diluent can be intermittently or continuously removed from the reactor where the volatile components are separated from the polymer and recycled, optionally after a distillation, to the reactor. The liquid diluent employed in the polymerization medium can be an alkane having from 3 to 7 carbon atoms, such as, for example, a branched alkane. The medium employed should be liquid under the conditions of polymerization and relatively inert. When a propane medium is used the process should be operated above the reaction diluent critical temperature and pressure. A hexane, isopentane, or isobutane medium can be employed. The slurry can be circulated in a continuous loop system.

The product polyethylene can have a melt index ratio (MIR or $I_{21}/I_2$) ranging from about 10 to less than about 300, or, in many embodiments, from about 15 to about 150. Flow index (FI, HLMI, or $I_{21}$ can be measured in accordance with ASTM D1238 (190° C., 21.6 kg). The melt index (MI, $I_2$) can be measured in accordance with ASTM D1238 (at 190° C., 2.16 kg weight).

Density can be determined in accordance with ASTM D-792. Density is expressed as grams per cubic centimeter (g/cm$^3$) unless otherwise noted. The polyethylene can have a density ranging from a low of about 0.89 g/cm$^3$, about 0.90 g/cm$^3$, or about 0.91 g/cm$^3$ to a high of about 0.95 g/cm$^3$, about 0.96 g/cm$^3$, or about 0.97 g/cm$^3$. The polyethylene can have a bulk density, measured in accordance with ASTM D1895 method B, of from about 0.25 g/cm$^3$ to about 0.5 g/cm$^3$. For example, the bulk density of the polyethylene can range from a low of about 0.30 g/cm$^3$, about 0.32 g/cm$^3$, or about 0.33 g/cm$^3$ to a high of about 0.40 g/cm$^3$, about 0.44 g/cm$^3$, or about 0.48 g/cm$^3$.

The polyethylene can be suitable for such articles as films, fibers, nonwoven and/or woven fabrics, extruded articles, and/or molded articles. Examples of films include blown or cast films formed in single layer extrusion, coextrusion, or lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets. Examples of fibers include melt spinning, solution spinning and melt blown fiber operations for use in woven or non-woven form to make filters, diaper fabrics, hygiene products, medical garments, geotextiles, etc. Examples of extruded articles include tubing, medical tubing, wire and cable coatings, pipe, geomembranes, and pond liners. Examples of molded articles include single and multi-layered constructions by injection molding or rotation molding or blow molding processes in the form of bottles, tanks, large hollow articles, rigid food containers and toys, etc.

EXAMPLES

All reactions were carried out under a purified nitrogen atmosphere in a glovebox. All solvents used were anhydrous and were sparged with nitrogen and stored over a drying agent such as alumina or molecular sieves. Organic starting materials were purchased from Aldrich and used as received. The 2-(1-Adamantyl)-p-cresol was prepared according to the procedure of Gademann, K.; Chavez, D. E.; Jacobsen, E. N. Angew. Chem. Int. Ed. 2002, 41, 3059. 1,3-bis(2-iodophenoxy)propane was prepared using the procedure in International Patent Application Publication No. 2003/091262. The procedure was modified by the substitution of 2-iodophenol for 2-bromophenol. Benzene-$d_6$ and THF-$d_8$ were purchased from Cambridge Isotope Labs, sparged with nitrogen, and stored over molecular sieves or alumina. $^1$H NMR spectra were obtained on a Bruker Avance III 400 MHz instrument.

Representative Synthetic Examples

A scheme for protecting a phenol group with 3,4-dihydro-2H-pyran, including a quenching step, is shown in reaction (2).

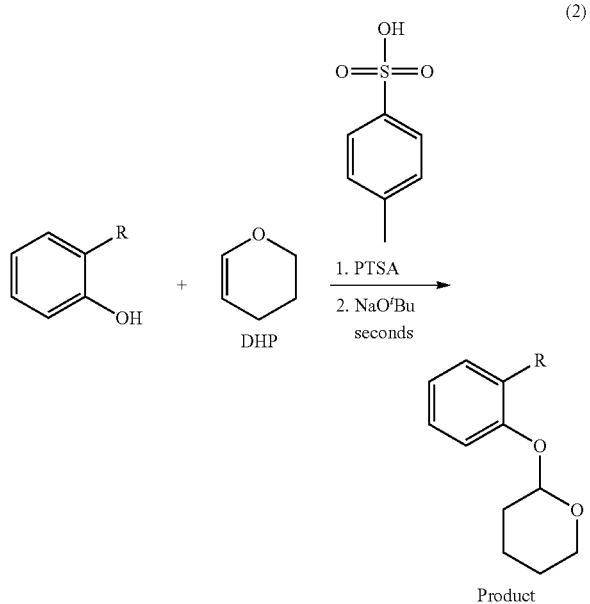

1a. Preparation of 2-(biphenyl-2-yloxy)tetrahydro-2H-pyran (Base Quench)

2-phenylphenol (1.85 g, 10.9 mmol) was dissolved in $CH_2Cl_2$ (ca. 10 mL) and PTSA (ca. 30 mg) added. DHP (2.1 g, 25.0 mmol) was added in 1 portion, causing the solvent to reflux. After about 10 seconds the color began to change from colorless to blue/brown. NaO$^t$Bu (ca. 200 mg) was added to quench the reaction as described in embodiments herein. During quenching, the color changed to a light yellow/orange. Volatiles were removed under vacuum and the material was extracted with pentane (ca. 10 mL), filtered, and dried under vacuum to yield a slightly cloudy oil.

FIG. 1 is a plot showing the proton nuclear magnetic resonance ($^1$H NMR; 400 MHz; $C_6D_6$) spectrum obtained for the 2-(biphenyl-2-yloxy)tetrahydro-2H-pyran. The NMR peaks were at δ 7.62 (m, 2H), 7.34 (m, 2H), 7.26 (m, 2H), 7.15 (m, 2H, overlaps $C_6D_5H$), 6.93 (m, 1H), 5.26 (s, 1H), 3.66 (m, 1H), 3.33 (m, 1H), 1.70-1.05 (m, 7H).

1b. Preparation of 2-(biphenyl-2-yloxy)tetrahydro-2H-pyran (Base Quench)

2-phenylphenol (5.7 g, 33.5 mmol) was dissolved in $CH_2Cl_2$ (ca. 25 mL) and PTSA (ca. 100 mg) added, the PTSA did not all dissolve. DHP (5.7 g, 68 mmol) was rapidly added, the PTSA dissolved. After about 10 seconds the solution began to darken. NaO$^t$Bu (ca. 200 mg) was added and the color changed to a light yellow. Volatiles were removed under vacuum at 50° C. and the material was extracted with pentane (ca. 25 mL), filtered, and dried under vacuum at 50° C. to yield a light yellow oil. The $^1$H NMR showed extremely clean product.

1c. Preparation of 2-(biphenyl-2-yloxy)tetrahydro-2H-pyran (Control: No Base Quench)

2-phenylphenol (20.1 g, 118 mmol) was dissolved in $CH_2Cl_2$ (200 mL) and PTSA (ca. 10 mg) added. DHP (10.2 g, 121 mmol) was added in 1 mL portions over five minutes. The reaction became warm. After about 20 minutes a faint blue color was noted. After stirring overnight there was some unreacted 2-phenylphenol as determined by $^1$H NMR. An additional 2.5 g of DHP and a small amount of PTSA was added. After stirring 4 h at room temperature, the $^1$H NMR showed that additional conversion had taken place but there was still unreacted 2-phenylphenol. The reaction was stirred over the weekend, and the $^1$H NMR showed that there was more 2-phenylphenol than was previously present.

1d. Preparation of 2-(biphenyl-2-yloxy)tetrahydro-2H-pyran (Control: No Base Quench)

2-phenylphenol (20.5 g, 120 mmol) was dissolved in $CH_2Cl_2$ (45 mL) and PTSA (ca. 15 mg) added. DHP (11.1 g, 132 mmol) was then added in 10 portions over several minutes. The reaction became warm. After about 5 hours stirring the reaction was checked and there was a ratio of product to the 2-phenylphenol starting material of 1.0 to 0.2. After stirring overnight it was clear that further decomposition had taken place.

1e. Preparation of 2-(biphenyl-2-yloxy)tetrahydro-2H-pyran (Control: No Base Quench)

2-phenylphenol (2.09 g, 12.3 mmol) was dissolved in $CH_2Cl_2$ (6 mL) and PTSA (ca. 35 mg) added. DHP (1.3 mL) was added in 1 portion, the reaction refluxed, after 20 min it had become dark.

1f. Preparation of 2-(biphenyl-2-yloxy)tetrahydro-2H-pyran (Control: No Base Quench)

2-phenylphenol (2.20 g, 12.9 mmol) was dissolved in $CH_2Cl_2$ (ca. 10 mL) and PTSA (ca. 4 mg) added. DHP (1.09 g, 13.0 mmol) was added in 1 portion; the reaction was stirred for about 2 min then turned light purple. Pyridine (ca. 0.25 mL) was added and the solution turned light yellow. Volatiles were removed under vacuum and the material was extracted with pentane (ca. 10 mL), filtered, and dried under vacuum. The $^1$H NMR showed reasonably clean product with impurities such as pyridine and some unreacted 2-phenylphenol. After heating at 60° C. for 4 hours the $^1$H NMR showed that only product and 2-phenylphenol were present, however the amount of 2-phenylphenol present had increased.

2a. Preparation of 2-(2-tert-butyl-4-methylphenoxy)tetrahydro-2H-pyran (Base Quench)

A 100 mL round bottom flask was charged with 2-tert-butyl-4-methylphenol (5.00 g, 30.4 mmol) and 30 mL of dichloromethane. To this stirring yellow solution was added para-toluenesulfonic acid monohydrate (0.091 g, 0.48 mmol) in one portion as a neat solid, not all of which dissolved immediately. After an additional minute of stirring following the acid addition, 3,4-dihydro-2H-pyran (5.12 g, 60.9 mmol) was added to the reaction flask rapidly in one aliquot. Within seconds the yellow color of the reaction began to fade and then darken to a red color. As soon as the red color was observed, solid sodium tert-butoxide (0.173 g, 1.8 mmol) was added to quench the reaction. Volatiles were then removed under reduced pressure at 50° C. and the crude material was extracted with 60 mL of pentane, filtered over Celite, and pumped down to yield 7.12 g of a pure, pale yellow solid (94%).

Figure 2:
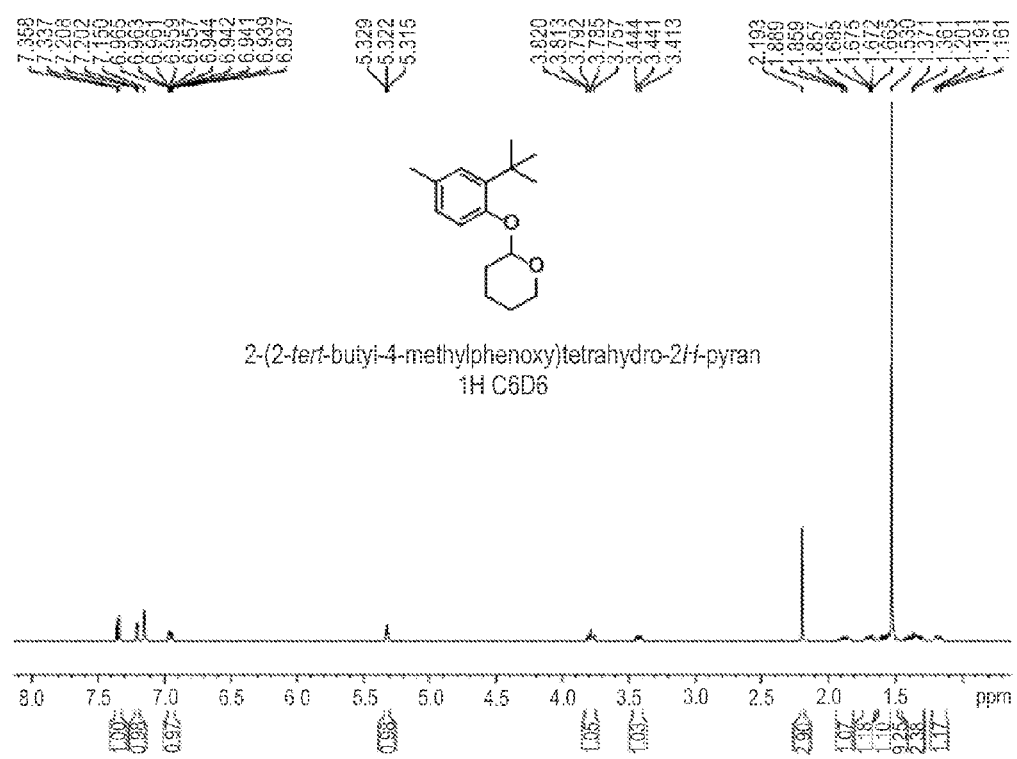
FIG. 2 is a plot showing the proton nuclear magnetic resonance ($^1$H NMR; 400 MHz; $C_6D_6$) spectrum obtained for the 2-(2-tert-butyl-4-methylphenoxy)tetrahydro-2H-pyran.

FIG. 2 is a plot showing the proton nuclear magnetic resonance ($^1$H NMR; 400 MHz; $C_6D_6$) spectrum obtained for the 2-(2-tert-butyl-4-methylphenoxy)tetrahydro-2H-pyran. The NMR peaks were at δ 7.35 (d, 1H, J=8.4 Hz), 7.20 (d, 1H, J=2.4 Hz), 6.95 (m, 1H), 5.32 (t, 1H, J=2.8 Hz), 3.79 (td, 1H, J=11.2, 2.8 Hz), 3.43 (m, 1H), 2.19 (s, 3H), 1.87 (m, 1H), 1.68 (m, 1H), 1.55 (m, 1H), 1.53 (s, 9H), 1.44-1.29 (m, 2H), 1.88 (m, 1H).

2b. Preparation of 2-(2-tert-butyl-4-methylphenoxy) tetrahydro-2H-pyran (Control: No Base Quench)

A 100 mL round bottom flask was charged with 2-tert-butyl-4-methylphenol (0.500 g, 3.04 mmol) and 30 mL of dichloromethane. To this stirring yellow solution was added para-toluenesulfonic acid monohydrate (0.0075 g, 0.039 mmol) in one portion as a neat solid, not all of which dissolved immediately. After an additional minute of stirring following the acid addition, 3,4-dihydro-2H-pyran (0.256 g, 3.04 mmol) was added to the reaction flask rapidly in one aliquot. After 17 hours of stirring at room temperature, the reaction had darkened in color. At this point $^1$H NMR ($C_6D_6$) of the crude reaction confirmed the presence of 3 aromatic species: product 2-(2-tert-butyl-4-methylphenoxy) tetrahydro-2H-pyran (25%), one with spectral resonances similar to, but not exactly the same as, the starting material 2-tert-butyl-4-methylphenol (38%), and an as yet to be identified species (37%).

3. Preparation of 2-(2-(1-Adamantyl)-4-methylphenoxy)tetrahydro-2H-pyran (Base Quench)

A 100 mL round bottom flask was charged with 2-(1-Adamantyl)-p-cresol (5.00 g, 20.6 mmol) and 30 mL of dichloromethane. To this stirring solution was added para-toluenesulfonic acid monohydrate (0.061 g, 0.32 mmol) in one portion as a neat solid, not all of which dissolved immediately. After an additional minute of stirring following the acid addition, 3,4-dihydro-2H-pyran (3.47 g, 41.3 mmol) was added to the reaction flask rapidly in one aliquot. Within approximately thirty seconds, the colorless reaction had turned yellow and a red hue developed. As soon as the red color was observed, solid sodium tert-butoxide (0.117 g, 1.2 mmol) was added to quench the reaction. Volatiles were then removed under reduced pressure at 50° C. and the crude material was extracted with 125 mL of pentane, filtered over Celite, and pumped down. At this point the material was washed with pentane (8 mL) and dried under reduced pressure to yield 4.46 g of off-white solid (67%). Additional material was collected by cooling the pentane wash to -35° C.

Figure 3:
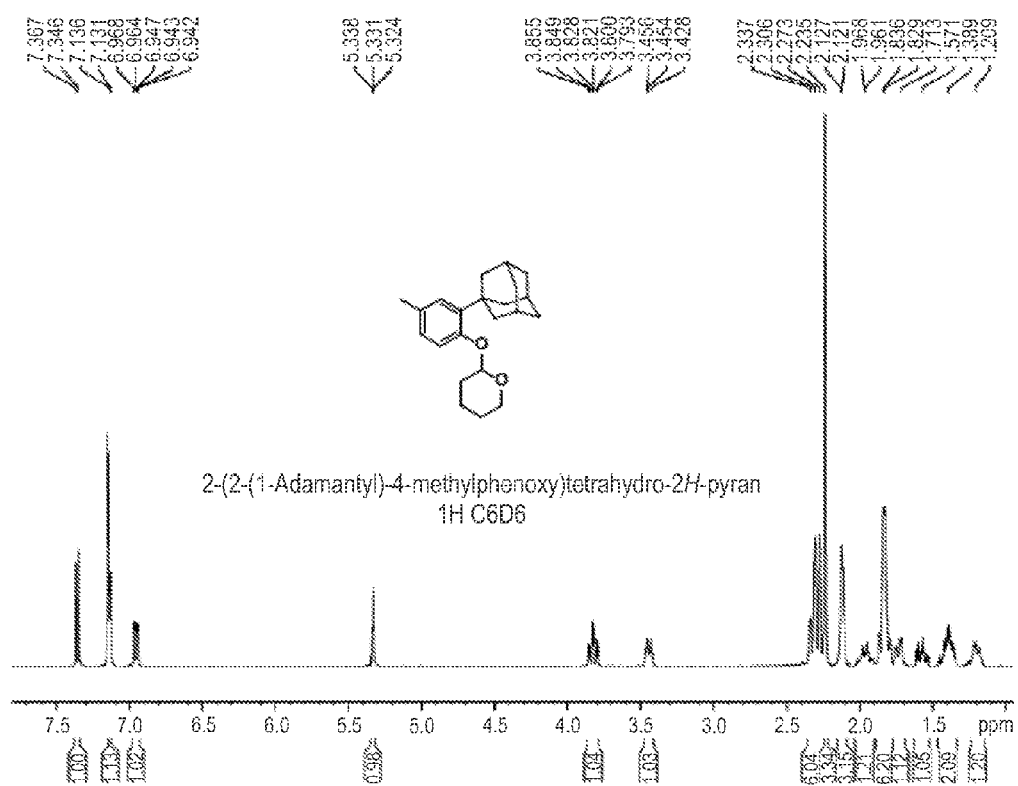
FIG. 3 is a plot showing the proton nuclear magnetic resonance ($^1$H NMR; 400 MHz; $C_6D_6$) spectrum obtained for the 2-(2-(1-Adamantyl)-4-methylphenoxy)tetrahydro-2H-pyran.

FIG. 3 is a plot showing the proton nuclear magnetic resonance ($^1$H NMR; 400 MHz; $C_6D_6$) spectrum obtained for the 2-(2-(1-Adamantyl)-4-methylphenoxy)tetrahydro-2H-pyran. The NMR peaks were at δ 7.35 (d, 1H, J=8 Hz), 7.13 (d, 1H, J=2 Hz), 6.96 (dd, 1H, J=2, 8 Hz), 5.33 (t, 1H, J=3 Hz), 3.82 (td, 1H, J=3, 11 Hz), 3.44 (m, 1H), 2.29 (q, 6H, J=13 Hz), 2.24 (s, 3H), 2.12 (m, 3H), 2.0-1.9 (m, 1H), 1.83 (m, 6H), 1.77-1.69 (m, 1H), 1.63-1.52 (m, 1H), 1.47-1.34 (m, 2H), 1.2 (m, 1H).

4. Preparation of 2-phenoxytetrahydro-2H-pyran (Base Quench)

A 100 mL round bottom flask was charged with phenol (5.0 g, 53 mmol) and 40 mL of dichloromethane. To this stirring solution was added para-toluenesulfonic acid monohydrate (0.158 g, 0.828 mmol) in one portion as a neat solid, not all of which dissolved immediately. After an additional minute of stirring following the acid addition, 3,4-dihydro-2H-pyran (8.9 g, 106 mmol) was added to the reaction flask rapidly in one aliquot; resulting in an exotherm and some refluxing. Seconds later the reaction began to turn red. Solid sodium tert-butoxide (0.301 g, 3.13 mmol) was added immediately in one portion to quench the reaction. Volatiles were then removed under reduced pressure at 60° C. and the crude material was extracted with 60 mL of pentane, filtered over Celite, and pumped down. Obtained 8.29 g of a yellow-orange oil.

Figure 4:
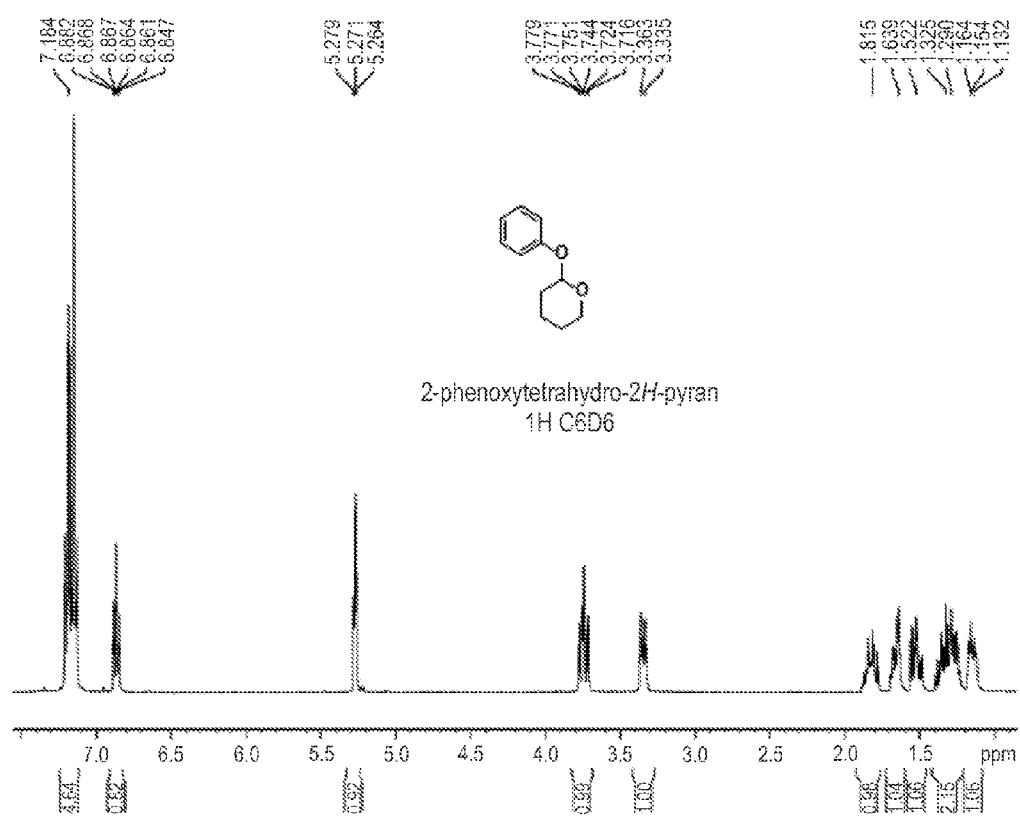
FIG. 4 is a plot showing the proton nuclear magnetic resonance ($^1$H NMR; 400 MHz; $C_6D_6$) spectrum obtained for the 2-phenoxytetrahydro-2H-pyran.

FIG. 4 is a plot showing the proton nuclear magnetic resonance ($^1$H NMR; 400 MHz; $C_6D_6$) spectrum obtained for the 2-phenoxytetrahydro-2H-pyran. The NMR peaks were at δ 7.22-7.11 (m, 4H), 6.86 (tt, 1H, J=1.2, 7.0 Hz), 5.27 (t, 1H, J=3.0 Hz), 3.75 (td, 1H, J=3.2, 11.0 Hz), 3.35 (m, 1H), 1.89-1.77 (m, 1H), 1.69-1.62 (m, 1H), 1.57-1.47 (m, 1H), 1.40-1.23 (m, 2H), 1.19-1.10 (m, 1H).

The use of protected phenol reagents to form compounds.

As described herein, THP protected phenols may be used to form ligands, or other compounds, in reactions that would otherwise attack the ligands. The formation of a representative compound, which may be used as a ligand in a catalyst system, is presented in reactions (3)-(5). The compounds are not limited to catalyst ligands, as any number of syntheses may take advantage of the high yield for the protected phenol.

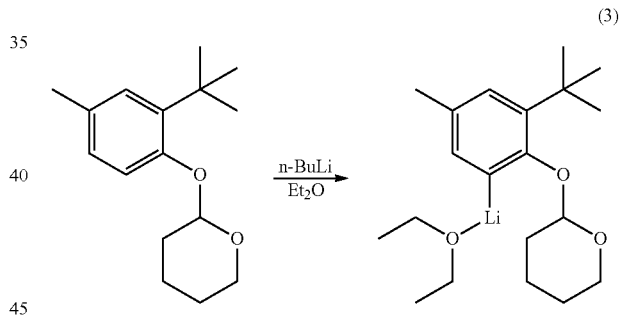

(3)

Step 1. Lithiation of 2-(2-tert-butyl-4-methylphenoxy)tetrahydro-2H-pyran (Reaction (3))

A 1.6 M solution of n-butyllithium in hexanes (7.5 mL, 0.012 mol) was added drop wise to a stirring solution of 2-(2-tert-butyl-4-methylphenoxy)tetrahydro-2H-pyran in 20 mL of diethyl ether. Within 10 minutes precipitate was evident and the reaction was allowed to stir at room temperature for 19 hours. After this time the solids were isolated on a sintered glass frit, washed with cold diethyl ether (-35° C., 2×10 mL), and dried under reduced pressure to yield 2.85 g of pale yellow powder (72%).

Figure 5:
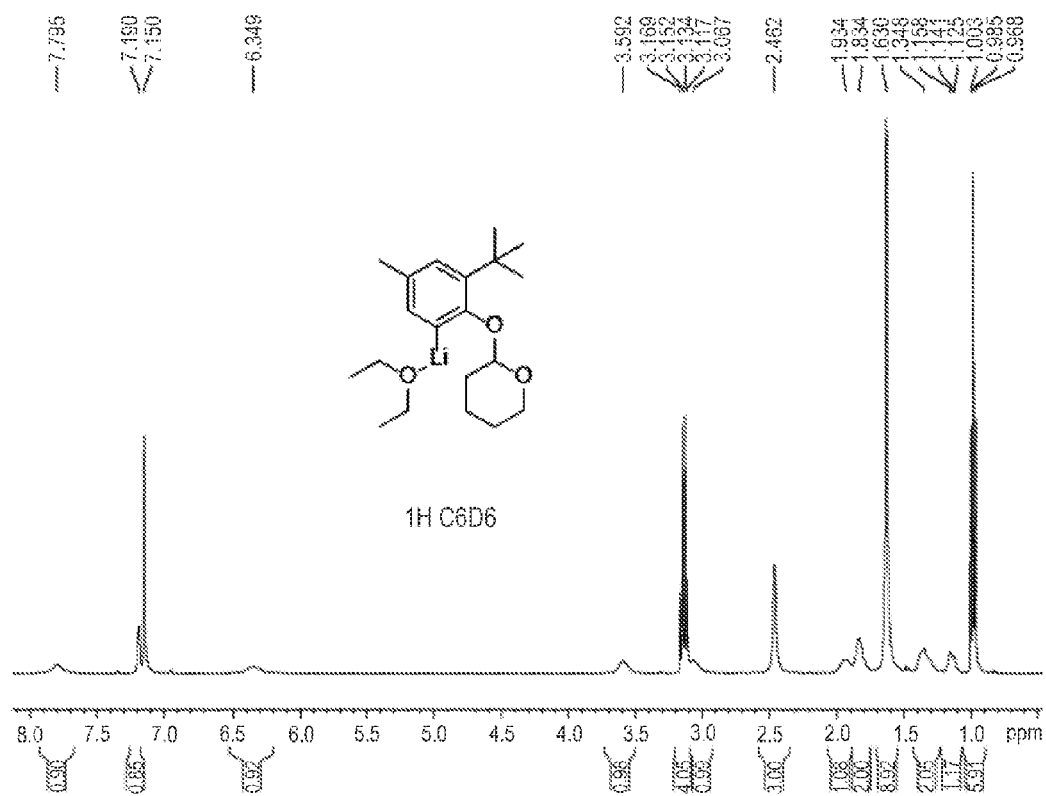
FIG. 5 is a plot showing the $^1$H NMR (400 MHz; $C_6D_6$) spectrum obtained for the of 2-(2-tert-butyl-4-methylphenoxy)tetrahydro-2H-pyran.

FIG. 5 is a plot showing the $^1$H NMR (400 MHz; $C_6D_6$) spectrum obtained for the lithiated 2-(2-tert-butyl-4-methylphenoxy)tetrahydro-2H-pyran. The NMR peaks were at δ 7.80 (br s, 1H), 7.19 (s, 1H), 6.35 (br s, 1H), 3.59 (br s, 1H), 3.14 (quartet, 4H, J=7.2 Hz), 3.07 (br s, 1H), 2.46 (s, 3H), 1.93 (br s, 1H), 1.83 (s, 2H), 1.63 (s, 9H), 1.35 (m, 2H), 1.17 (br s, 1H), 0.99 (t, 6H, J=7.2 Hz).

(4)

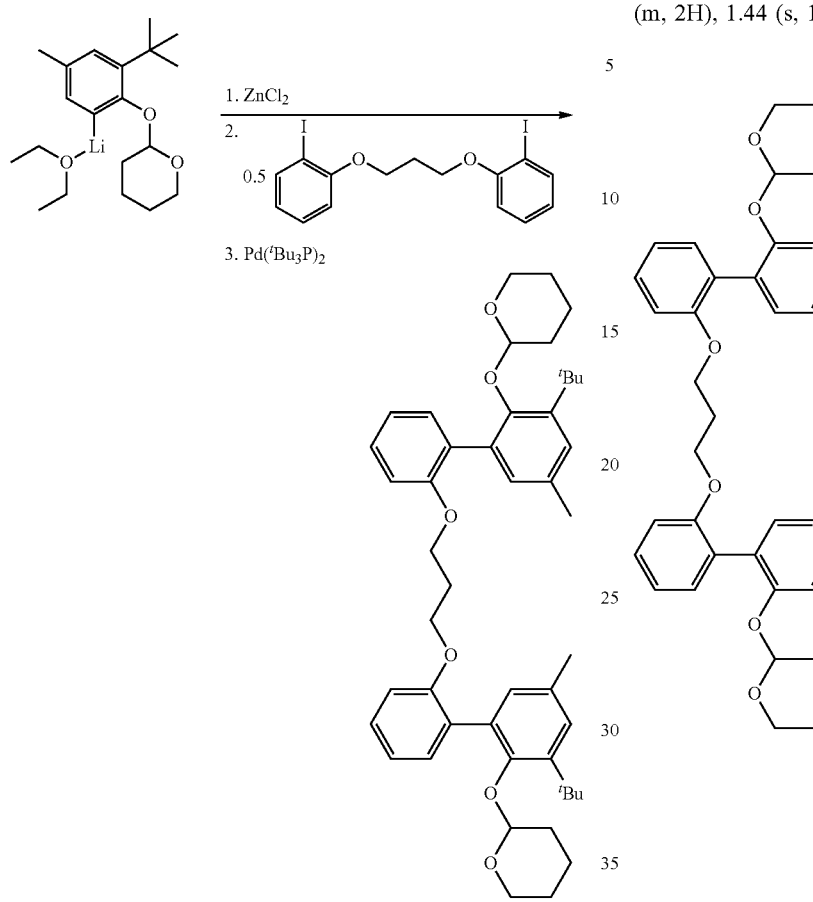

7.07 (s, 3H), 7.00-6.67 (m, 6H), 4.37 (s, 2H), 4.20-3.83 (m, 4H), 3.66 (br s, 2H), 2.93 (m, 2H), 2.31-2.15 (m, 6H), 1.53 (m, 2H), 1.44 (s, 18H), 1.37-1.06 (m, 9H), 0.93 (m, 2H).

(5)

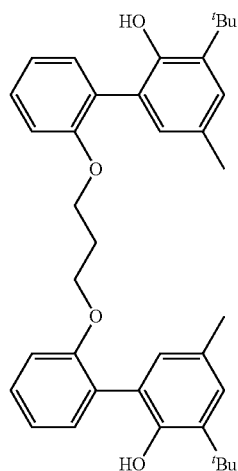

Step 2. Negishi Coupling (Reaction (4))

The lithiated, protected phenol from step 1 (1.0 g, 3.04 mmol) was stirred in 20 mL of THF. To this solution was added a 5 mL THF solution of ZnCl$_2$ (0.415 g, 3.04 mmol) drop wise. Once addition was complete, the reaction was allowed to stir for an additional 30 minutes at room temperature. After this time, bis(2-iodophenoxy)propane (0.730 g, 1.52 mmol) and Pd($^t$Bu$_3$P)$_2$ (0.031 g, 0.0608 mmol) were added sequentially as 5 mL THF solutions. The reaction flask was then equipped with a reflux condenser (using a stream of N$_2$ as the coolant) and heated to 80° C. After 1.5 hours the color had noticeably darkened to brown and heating was continued for a total of 24 hours. After cooling, volatiles were removed under reduced pressure and the crude solids were extracted with 100 mL of diethyl ether, washed with water (2×100 mL), brine (1×100 mL), and dried over MgSO$_4$. The solution was then filtered over Celite and pumped down. Upon stirring the resulting solids in 20 mL of pentane, everything initially went into solution and shortly thereafter white solids began precipitating from solution. This material was isolated on a sintered glass frit, washed with a fresh aliquot of cold pentane (−35° C., 10 mL), and dried under reduced pressure. Obtained 0.434 g of a white powder (40%).

Figure 6:
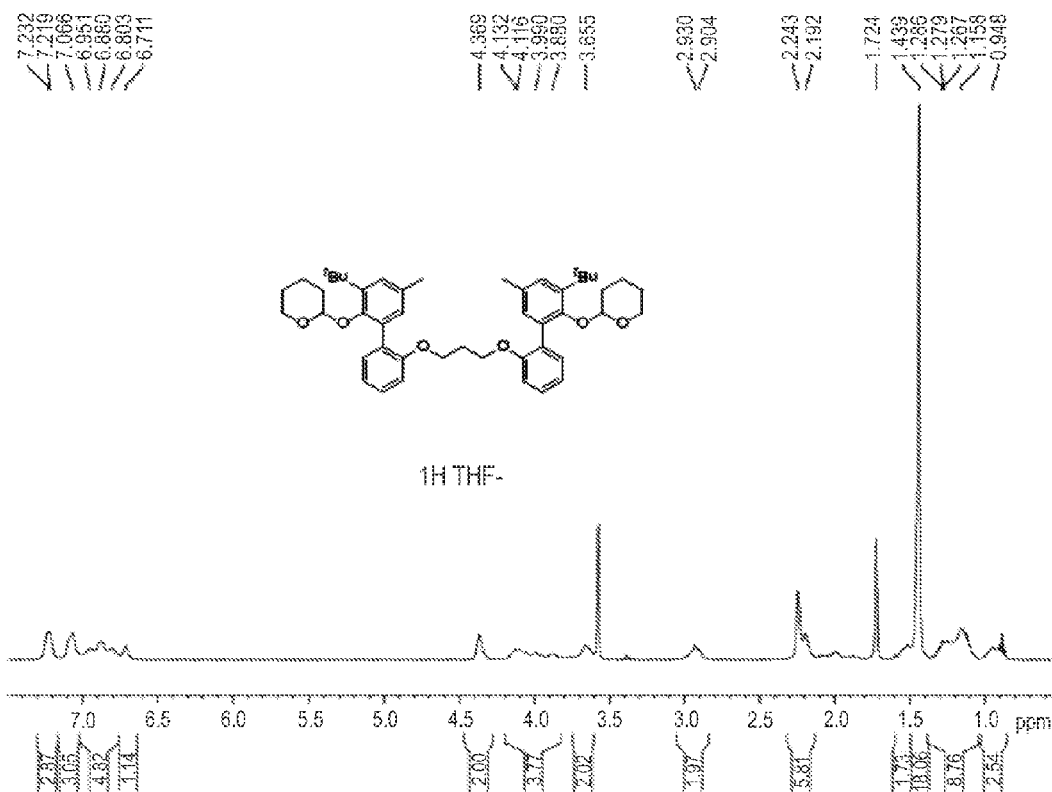
FIG. 6 is a plot showing the $^1$H NMR (400 MHz; $C_6D_6$) spectrum obtained for the phenol protected ligand product of the Negishi coupling.

FIG. 6 is a plot showing the $^1$H NMR (400 MHz; C$_6$D$_6$) spectrum obtained for the phenol protected product of the Negishi coupling. The NMR peaks were at δ 7.23 (s, 3H), Step 3. Deprotection (Reaction(5))

The protected ligand obtained from Step 2 (2.49 g, 3.45 mmol) was stirred at room temperature in 40 mL of a 1:1 CH$_2$Cl$_2$:MeOH solution. Para-toluenesulfonic acid monohydrate (0.066 g, 0.345 mmol) was added as a neat solid and stirring was continued for 24 hours. After removing volatiles under reduced pressure, the solids were extracted with pentane (40 mL), filtered, and volatiles were again removed under reduced pressure. The resulting solids were re-dissolved in pentane (20 mL) and the solution was placed in the freezer at −35° C. over the weekend. At this point the precipitated solid material was isolated, washed with cold pentane (−35° C., 20 mL), and dried under reduced pressure. The original mother liquor and pentane washing were combined, concentrated to a volume of 10 mL, and returned to the freezer. The next day a second crop of solids were isolated and both crops were combined, dried under reduced pressure, and washed vigorously with 10 mL of toluene at room temperature. After drying the toluene washed material under reduced pressure at 60° C., 0.794 g of a pure white powder was obtained (42%).

Figure 7:
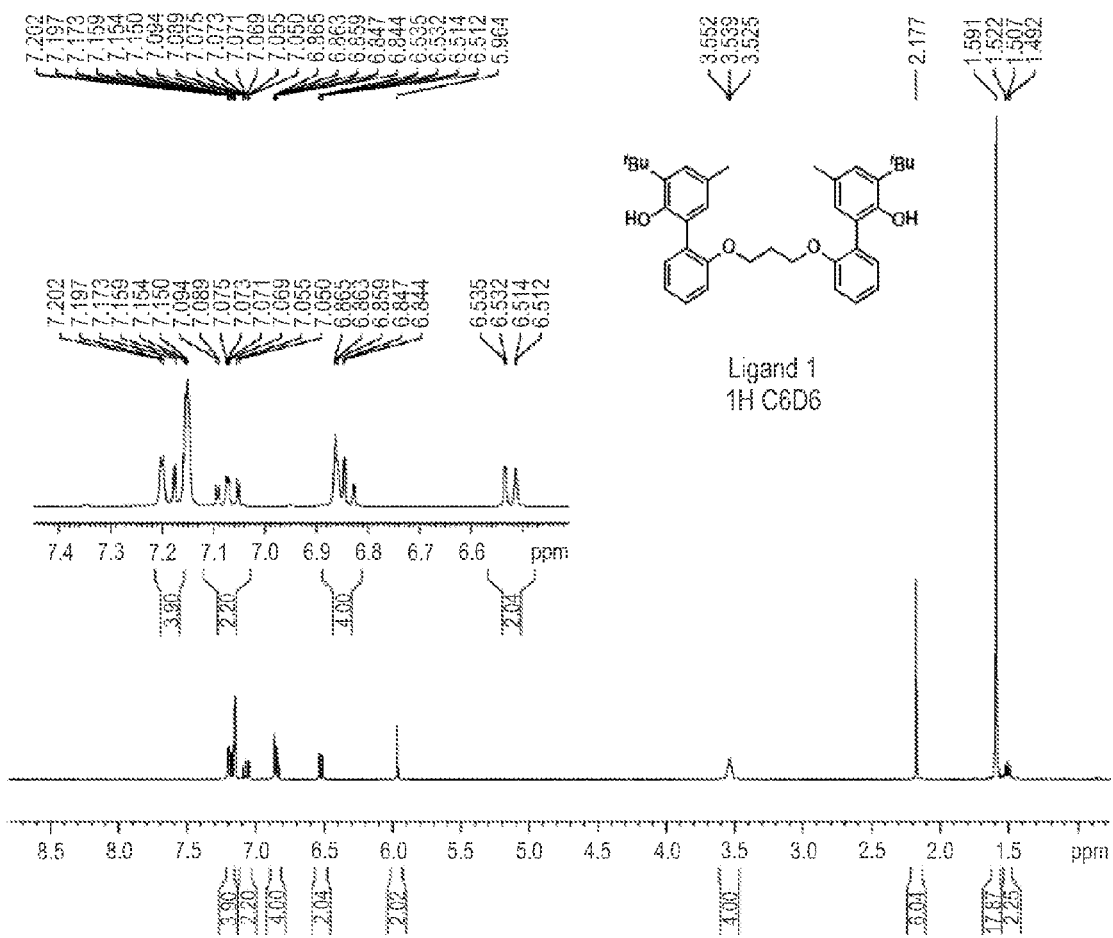
FIG. 7 is a plot showing the $^1$H NMR (400 MHz; $C_6D_6$) spectrum obtained for the product ligand.

FIG. 7 is a plot showing the $^1$H NMR (400 MHz; $C_6D_6$) spectrum obtained for the deprotected product ligand. The NMR peaks were at δ 7.18 (m, 4H, overlaps with solvent peak), 7.07 (m, 2H), 6.84 (m, 4H), 6.53 (dd, 2H, J=1, 8 Hz), 5.96 (s, 2H), 3.53 (t, 4H, J=5.4 Hz), 2.18 (s, 6H), 1.59 (s, 18H), 1.51 (quintet, 2H, J=5.4 Hz).

While the foregoing is directed to embodiments of the present invention, other and further embodiments of the invention can be devised without departing from the basic scope thereof, and the scope thereof is determined by the claims that follow.

What is claimed is:

1. A method for protecting a phenol group on a precursor compound, comprising:
   reacting the phenol group with dihydropyran in an acid catalyzed protection reaction; and
   quenching the protection reaction with a strong base within about 60 seconds to form a protected precursor compound.

2. The method of claim 1, comprising:
   performing an additional reaction with the protected precursor compound and a reagent, wherein the reagent would attack an unprotected phenol group; and
   deprotecting the phenol group to form a product compound.

3. The method of claim 1, comprising quenching the reaction within about 10 seconds.

4. The method of claim 1, comprising quenching the reaction immediately after a first color change.

5. The method of claim 2, comprising using the product compound in further reactions to form a final product compound.

6. The method of claim 2, wherein the product compound is a pharmaceutical.

7. The method of claim 2, wherein the product compound is a catalyst.

8. The method of claim 2, wherein the product compound is a polymerization catalyst.

9. A method for forming a polymerization catalyst, comprising:
   reacting a phenol group on a precursor compound with dihydropyran to form a protected phenol precursor;
   quenching the reaction with a strong base within about 60 seconds;
   performing an additional reaction with the protected phenol precursor and a reagent to form a ligand precursor compound, wherein the reagent would attack an unprotected phenol group; and
   deprotecting the phenol on the ligand precursor compound.

10. The method of claim 9, comprising quenching the reaction within about 10 seconds.

11. The method of claim 9, comprising forming a ligand from the ligand precursor compound.

12. The method of claim 11, comprising forming a catalyst compound with the ligand.

13. The method of claim 12, comprising forming a spray dried catalyst.

14. The method of claim 12, comprising combining the catalyst compound with a metallocene catalyst to form a commonly supported catalyst system.

15. The method of claim 12, comprising combining the catalyst compound with a catalyst of the formula:

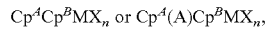

wherein M is a Group 4, 5, or 6 atom; $Cp^A$ and $Cp^B$ are each bound to M and are independently selected from the group consisting of cyclopentadienyl ligands, substituted cyclopentadienyl ligands, ligands isolobal to cyclopentadienyl and substituted ligands isolobal to cyclopentadienyl; (A) is a divalent bridging group bound to both $Cp^A$ and $Cp^B$ selected from the group consisting of divalent $C_1$ to $C_{20}$ hydrocarbyls and $C_1$ to $C_{20}$ heteroatom containing hydrocarbonyls, wherein the heteroatom containing hydrocarbonyls comprise from one to three heteroatoms; X is a leaving group selected from the group consisting of chloride ions, bromide ions, $C_1$ to $C_{10}$ alkyls, and $C_2$ to $C_{12}$ alkenyls, carboxylates, acetylacetonates, and alkoxides; and n is an integer from 1 to 3.

16. The method of claim 12, comprising combining the catalyst compound with a catalyst of the formula:

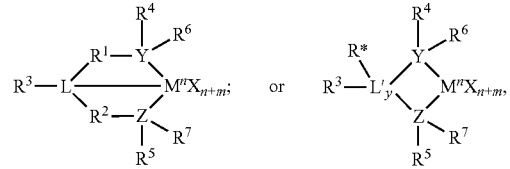

wherein M is a Group 3 to 12 transition metal or a Group 13 or 14 main group metal; each X is independently an anionic leaving group; y is 0 or 1; n is the oxidation state of M; m is the formal charge of the ligand represented by YZL or YZL'; L is a Group 15 or 16 element; L' is a group 15 or 16 element or Group 14 containing group; Y is a Group 15 element; Z is a Group 15 element; $R^1$ and $R^2$ are independently a $C_1$ to $C_{20}$ hydrocarbon group, a heteroatom containing group having up to twenty carbon atoms, silicon, germanium, tin, lead, or phosphorus; $R^1$ and $R^2$ may be interconnected to each other; $R^3$ is absent, a hydrocarbon group, hydrogen, a halogen, or a heteroatom containing group; $R^4$ and $R^5$ are independently an alky group, an aryl group, a substituted aryl group, a cyclic alkyl group, a substituted cyclic alkyl group, a cyclic aralkyl group, a substituted cyclic aralkyl group, or a multiple ring system; $R^4$ and $R^5$ may be interconnected to each other; $R^6$ and $R^7$ are independently absent, hydrogen, an alkyl group, a halogen, a heteroatom, or a hydrocarbyl group; and R* is absent, hydrogen, a Group 14 atom containing group, a halogen, or a heteroatom containing group.

17. The method of claim 12, comprising forming a catalyst that includes a non-metallocene comprising a ligand complexed to a metal through an oxygen atom.

18. The method of claim 12, comprising:
   supporting a non-metallocene on a catalyst support to form a supported catalyst; and
   adding a metallocene catalyst to the supported catalyst to form a commonly supported catalyst system.

19. A method for generating a polyethylene polymer, comprising reacting at least ethylene with a catalyst system comprising a catalyst formed by reacting a metal compound with a ligand, wherein the ligand is formed by:
   reacting a phenol group on a precursor compound with dihydropyran to form a protected phenol precursor;

quenching the reaction with a strong base within about 60 seconds;

performing an additional reaction with the protected phenol precursor and a reagent to form a ligand precursor compound, wherein the reagent would attack an unprotected phenol group; and deprotecting the phenol on the ligand precursor compound to form the ligand.

20. The method of claim 19, comprising adding a comonomer to the reaction of the ethylene with the catalyst system, wherein the comonomer comprises an alphaolefin having 4 to 8 carbon atoms.

* * * * *